United States Patent
Chang et al.

(10) Patent No.: US 8,256,427 B2
(45) Date of Patent: Sep. 4, 2012

(54) ENDOTRACHEAL TUBE HOLDER

(75) Inventors: Ya-Wen Chang, Taipei (TW);
Chien-Hui Yang, Taipei (TW); Yu-Jen Lin, Taipei (TW); Hai-Ling Lu, Taipei (TW); Han-Ping Wang, Taipei County (TW)

(73) Assignees: Mackay Memorial Hospital, Taipei (TW); Fortune Medical Instrument Corp., Taipei County (TW)

( * ) Notice: Subject to any disclaimer, the term of this patent is extended or adjusted under 35 U.S.C. 154(b) by 9 days.

(21) Appl. No.: 12/880,624

(22) Filed: Sep. 13, 2010

(65) Prior Publication Data

US 2011/0220127 A1    Sep. 15, 2011

(30) Foreign Application Priority Data

Mar. 9, 2010  (TW) ................ 99204132 U (51) Int. Cl.
*A61M 5/32* (2006.01)
*A61M 15/08* (2006.01)
*A61M 15/00* (2006.01)
*A61M 16/00* (2006.01)
*A62B 9/04* (2006.01)
*A62B 18/08* (2006.01)
*A61F 5/56* (2006.01)
*A61C 5/14* (2006.01)

(52) U.S. Cl. ............ 128/861; 128/200.24; 128/200.26; 128/207.14; 128/207.15; 128/207.16; 128/848; 128/859; 128/860; 128/202.27; 128/206.24; 128/207.17; 128/207.18; 604/174; 604/178

(58) Field of Classification Search ............ 128/200.24, 128/200.26, 207.14, 207.15, 207.16, 848, 128/859–861, 202.27, 206.24, 207.17, 207.18, 128/207.29, 912; 604/174, 178
See application file for complete search history.

(56) References Cited

U.S. PATENT DOCUMENTS

| 2,820,457 A | * | 1/1958 | Phillips | 128/200.26 |
| 4,449,527 A | * | 5/1984 | Hinton | 128/207.17 |
| 5,305,742 A | * | 4/1994 | Styers et al. | 128/207.17 |
| 5,806,516 A | * | 9/1998 | Beattie | 128/207.17 |
| 2009/0255538 A1 | * | 10/2009 | Thomson et al. | 128/207.17 |
| 2011/0214675 A1 | * | 9/2011 | Kost | 128/207.17 |

* cited by examiner

*Primary Examiner* — Patricia Bianco
*Assistant Examiner* — Nihir Patel
(74) *Attorney, Agent, or Firm* — WPAT, P.C.; Anthony King (57) ABSTRACT

An endotracheal tube holder is provided. The endotracheal tube holder includes an adjustable securing clamp, an adjusting unit, a bite block, and a securing strap. The adjustable securing clamp includes a first clamping unit having a first clamping portion, and a second clamping unit having a second clamping portion. The first clamping portion and the second clamping portion are oppositely and correspondingly aligned for holding an endotracheal tube. The adjusting unit includes an elastic member, coupled between the first clamping unit and the second clamping unit. The bite block is configured at one side of the first clamping portion and includes an endotracheal tube accommodation portion. The endotracheal tube accommodation portion covers over the endotracheal tube for providing a protection to the endotracheal tube. The securing strap includes two ends respectively coupled to two lateral sides of the first clamping unit.

28 Claims, 7 Drawing Sheets

ENDOTRACHEAL TUBE HOLDER

BACKGROUND OF THE INVENTION

1. Field of the Invention

The present invention relates generally to a securing member adapted for securing medical instruments, and more particularly to an endotracheal tube holder.

2. The Prior Arts

With respect to the medical purpose, endotracheal intubation is a process of inserting a plastic-made endotracheal tube into a trachea (lung) through patient's mouth to directly provide oxygen thereto. The endotracheal intubation treatment is not only capable of maintaining the airway unimpeded, but also adapted for providing high concentration oxygen for relieving patient's difficulty in breathing, or even feeding specific drugs through the endotracheal tube. The endotracheal intubation treatment may be applicable in many different situations, such as the patient is in unconsciousness (GCS<9) and is suspected of airway obstruction, or cardiac arrest, respiratory arrest, respiratory failure, pulmonary edema, or chronic airway obstruction.

After the endotracheal tube is inserted into patient's trachea, it should be secured. A conventional approach to secure the endotracheal tube is as following. At first, a medical tape is stuck at a securing position of the endotracheal tube as a mark. Then, an oral airway is provided for preventing the patient biting the endotracheal tube. Then, a cotton string is tied with a clove hitch for securing the endotracheal tube. The two sides of the cotton string are crossed to hitch the two ears of the patient, respectively. An additional 15 cm cotton string is provided through the two sides of the cotton string hitching the two ears of the patient, and is then tied with a hard knot over the patient's head. Further, $2\times 2$ $cm^2$ gauzes are provided at corners of the mouth for preventing injury caused to the skin under being pressed.

However, this conventional approach has many difficulties. For example, when the cotton string is tied with different manipulations, the positions compressed by the cotton string often vary. If the cotton string is too tightly tied, it would be difficult to untie the cotton string later, and often cause the patient feeling uncomfortable or even cause ulceration at the corners of patient's mouth. If the cotton string is too loosely tied, or the medical tape is not well cleaned, or the patient dribbles to wet the cotton string, the friction force between the cotton string and the endotracheal tube often decreases, so that the endotracheal tube may likely slip off from the cotton string. Further, if the patient dribbles too much, the gauzes provided at the corners of the mouth would be often wetted and should be frequently replaced. Furthermore, the position of the endotracheal tube where the medical tape is provided for positioning is configured with marking numbers. However, since the medical tape has to be frequently replaced, the marking numbers provided on the endotracheal tube may be worn out, thus causing inconvenience of the medical staff in determining whether or not the endotracheal tube is correctly positioned.

The purpose of providing the oral airway is for preventing the patient biting the endotracheal tube, and preventing failure of oxygen supplying through the endotracheal tube, thus maintaining the airway unimpeded. Although the positions in the mouth selected to bear the endotracheal tube are almost changed every day, when the endotracheal intubation treatment has become a routine treatment to a patient, ulcers are often caused in patient's mouth. Responsive thereto, the patient might not like to suffer the pain caused by the ulcers, or even become bad-tempered and agitated. The patient in bad temper might even try to remove the endotracheal tube by himself. Further, the total process of oral care and securing the endotracheal tube may take the nursing staff about 30 minutes. When the process is interrupted by other matter, the process may last a longer time. In this case, a bad-tempered patient is often reluctant to wait the nursing staff back, and tends to remove the endotracheal tube away by himself. However, such an unplanned extubation operation executed by the patient would probably cause serious respiratory complications, such as upper respiratory tract damage, bronchial spasm, or inhalation of intestinal contents. Further, the unplanned extubation may also cause respiratory failure, anoxia, or even death. Meanwhile, as a subsequence, a reapplication of the endotracheal tube has to be executed. However, such a reapplication of endotracheal tube in emergency is more dangerous, since it may possibly cause nosocomial pneumonia.

Therefore, a more effective endotracheal tube holder is very much desirable in this field.

SUMMARY OF THE INVENTION

For solving all of the foregoing-mentioned difficulties, the endotracheal tube is highly desired to be effectively secured.

Accordingly, an objective of the present invention is to provide an endotracheal tube holder, adapted for fast and effectively securing an endotracheal tube.

The present invention provides an endotracheal tube holder for solving all of the foregoing-mentioned difficulties. The endotracheal tube holder comprises an adjustable securing clamp and a securing strap.

The adjustable securing clamp comprises a first clamping unit, a second clamping unit, an adjusting unit, and a bite block. The first clamping unit has a first clamping portion and the second clamping unit has a second clamping portion. The first clamping portion and the second clamping portion are oppositely and correspondingly aligned with each other for holding an endotracheal tube. The adjusting unit comprises an elastic member coupled between the first clamping unit and the second clamping unit. The elastic member is adapted for providing an elastic adjustment between the corresponding alignment of the first clamping portion and the second clamping portion. The bite block is configured at one side of the first clamping portion. The bite block has an endotracheal tube accommodation portion. The endotracheal tube accommodation portion attaches to and covers over the endotracheal tube for providing a further protection to the endotracheal tube.

The securing strap has two ends respectively coupled to two lateral sides of the first clamping unit.

The present invention is applicable for endotracheal tubes of different sizes. In accordance with the present invention, the endotracheal tube can be secured without employing the cotton string. As such, the patient applied with the present invention would be cared cleaner. Further, the endotracheal tube holder is provided with a bite block function, thus effectively reducing the injury to patient's oral cavity and skins behind ears. The endotracheal tube holder is clinically applicable and convenient. The endotracheal tube holder of the present invention includes an adjusting unit configured as a push-on type spring adjusting unit, and can be operated by only one hand. Accordingly, the present invention is adapted to save the operation time. The present invention is also complied with the standard operation process, and is adapted for avoiding unplanned extubation, and is suitable for patients using different kinds of endotracheal tubes. Specifically, the present invention has the following advantages:

1. Regarding patients, the present invention is adapted for reducing injury to the oral mucosa and possibility of causing mouth cavity ulcer. The endotracheal tube of the present invention is adapted to achieve a better insulation protection for improving the mouth cavity ulcer, and reducing or preventing unnecessary injury to the oral mucosa, thus relieving pains or discomfortableness;

2. Regarding the nursing staff, the endotracheal tube can be operated by a single hand, and therefore providing more convenience to the nursing staff for nursing the patients.

3. Regarding the adaptability, the present invention can be adaptively applied in clinical practice, for improving the comfortableness of the patients, reducing injuries caused to the oral mucosa. Further, the patients and their family members would be more satisfactory for the medical service facilitated by the endotracheal tube according to the present invention. As such, the present invention provides a more convenient service to the patient's caregiver.

The present invention is further explained in the following embodiment illustration and examples. Those examples below should not, however, be considered to limit the scope of the invention, it is contemplated that modifications will readily occur to those skilled in the art, which modifications will be within the spirit of the invention and the scope of the appended claims.

BRIEF DESCRIPTION OF THE DRAWINGS

The present invention will be apparent to those skilled in the art by reading the following detailed description of preferred embodiments thereof, with reference to the attached drawings, in which.

DETAILED DESCRIPTION OF THE PREFERRED EMBODIMENT

The accompanying drawings are included to provide a further understanding of the invention, and are incorporated in and constitute a part of this specification. The drawing illustrates embodiments of the invention and, together with the description, serves to explain the principles of the invention.

Figure 1:
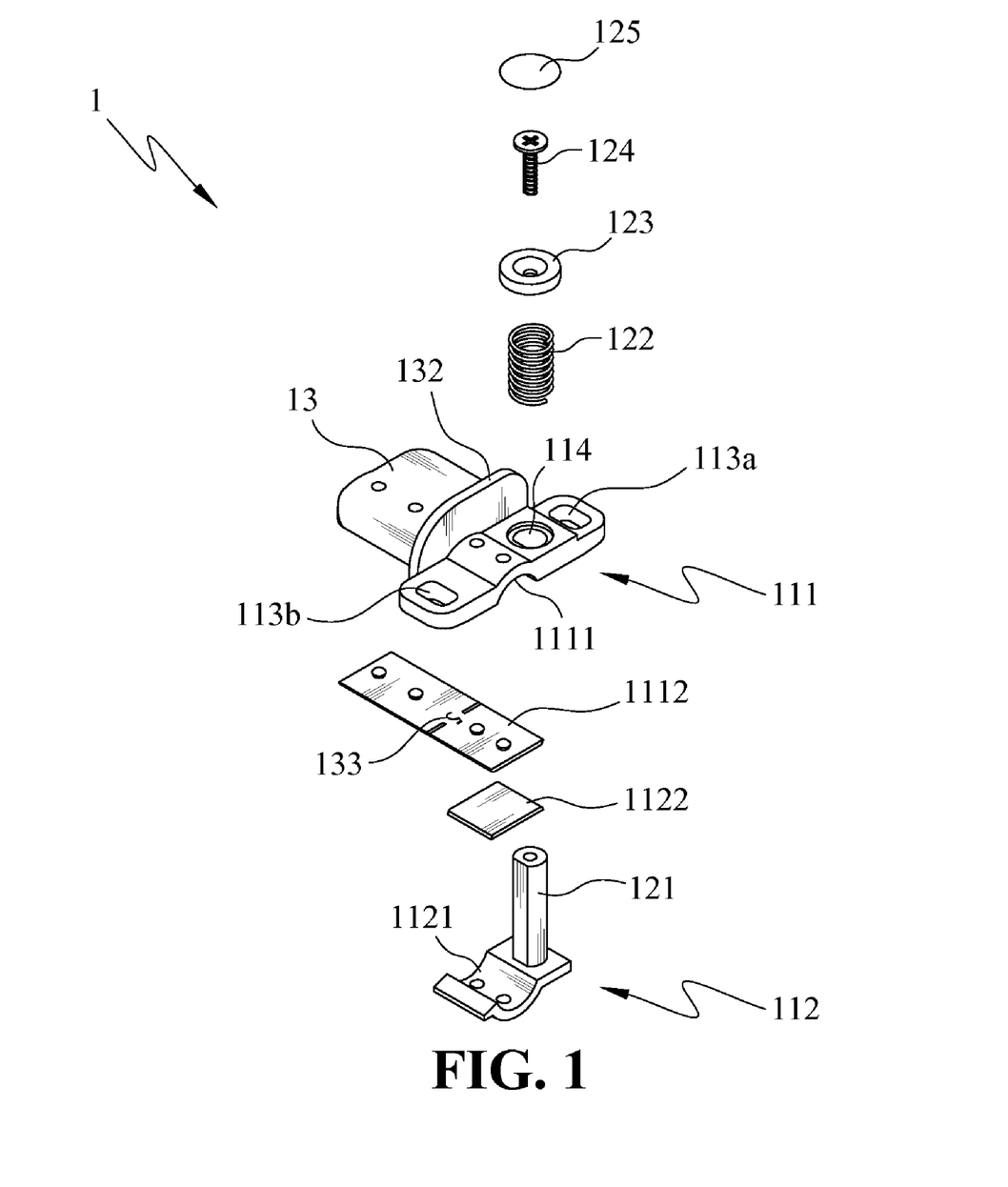
FIG. 1 is an exploded view of an adjustable securing clamp of the endotracheal tube holder according to an embodiment of the present invention.
Figure 2:
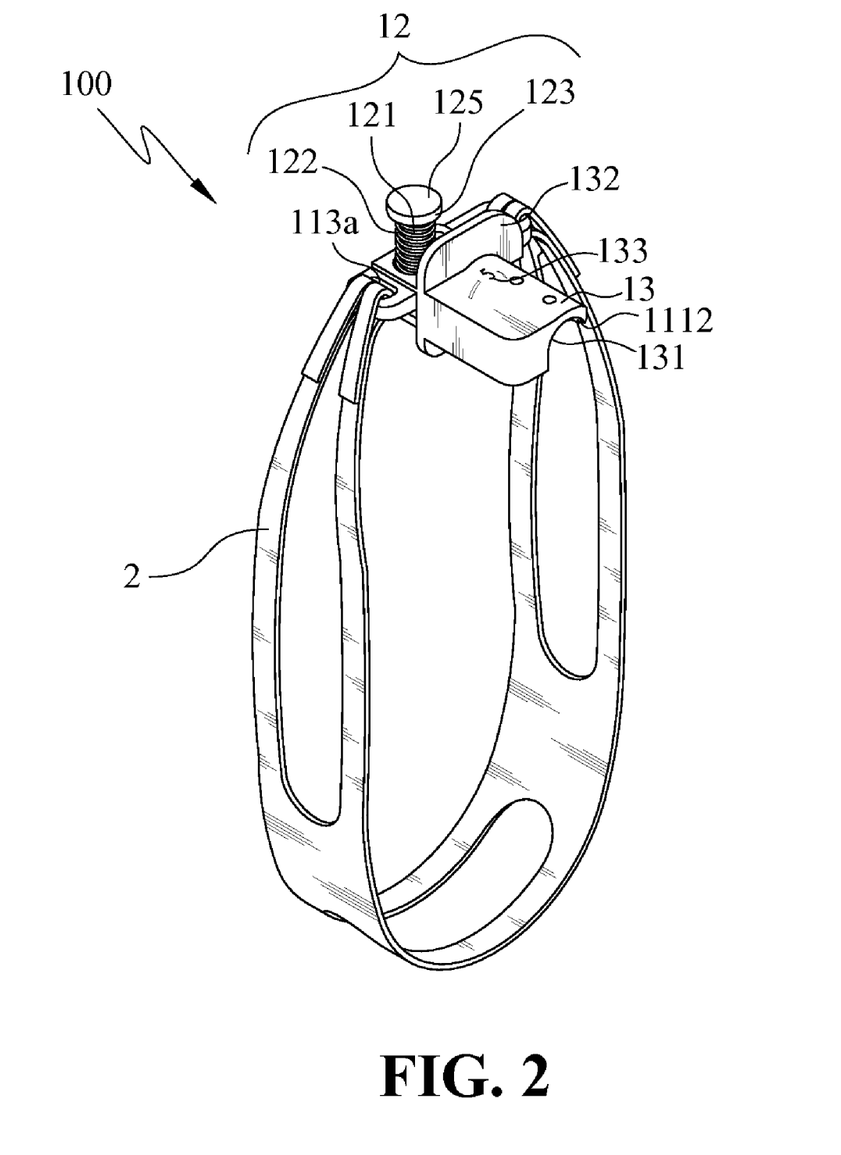
FIG. 2 is a perspective view of the endotracheal tube holder according to a preferred embodiment of the present invention.
Figure 3:
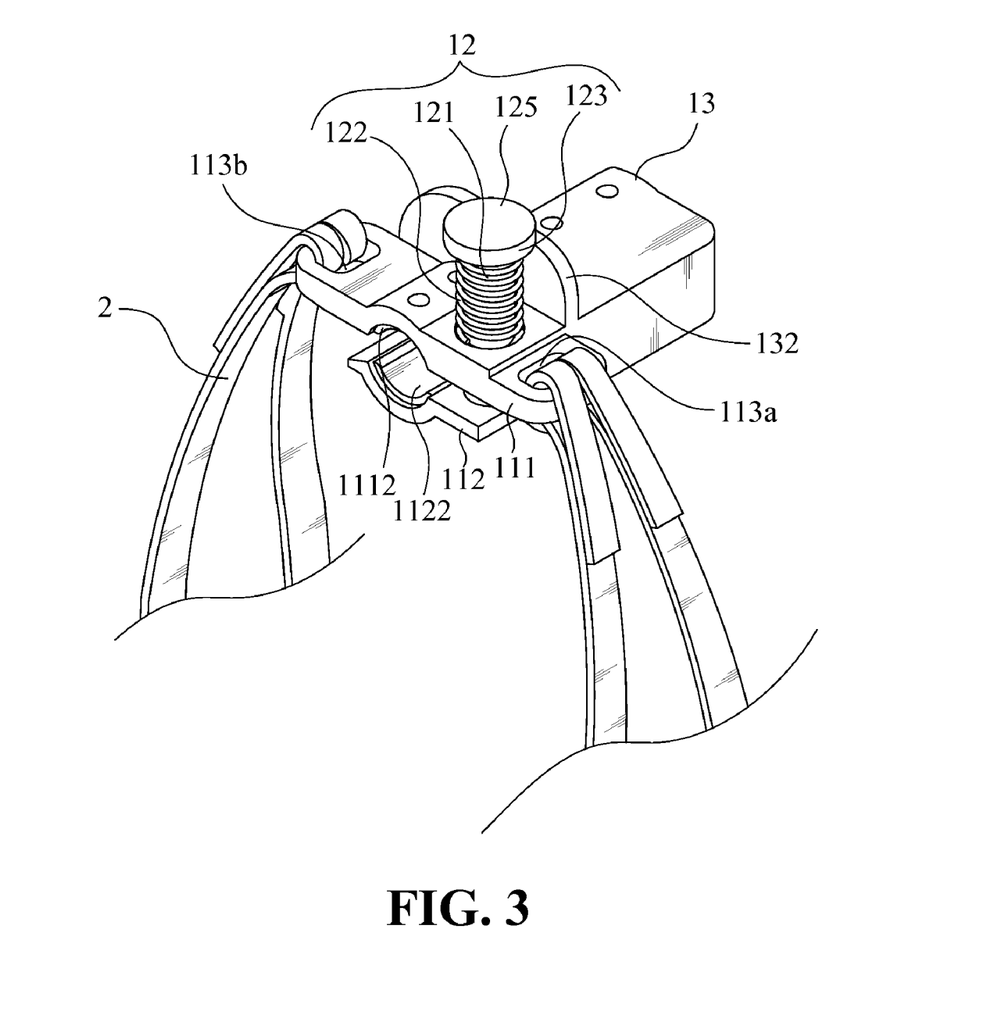
FIG. 3 is a partial enlarged perspective view of the endotracheal tube holder according to a preferred embodiment of the present invention.
Figure 4:
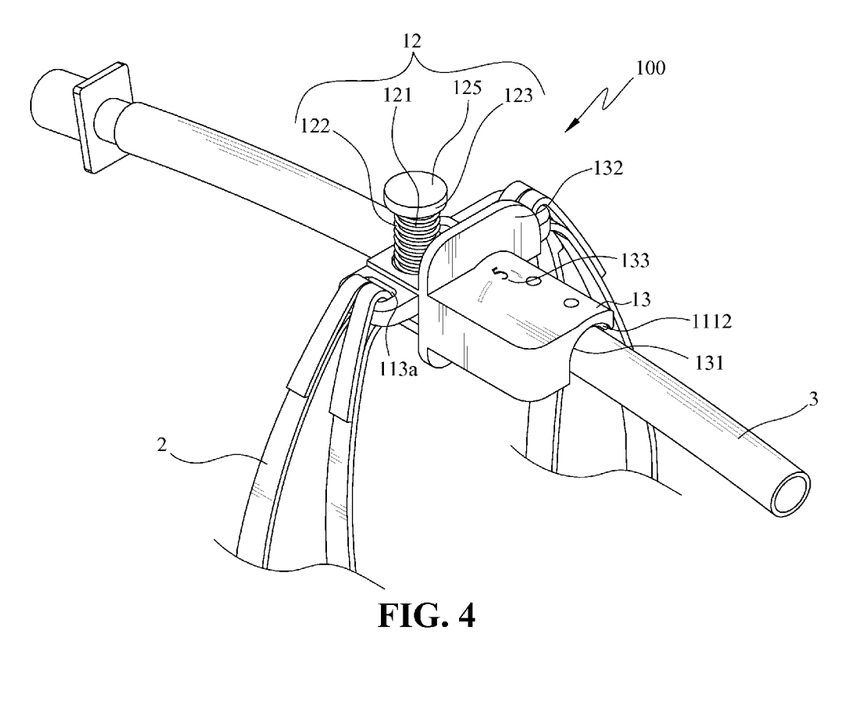
FIG. 4 is a perspective view of the endotracheal tube holder holding an endotracheal tube.
Figure 5:
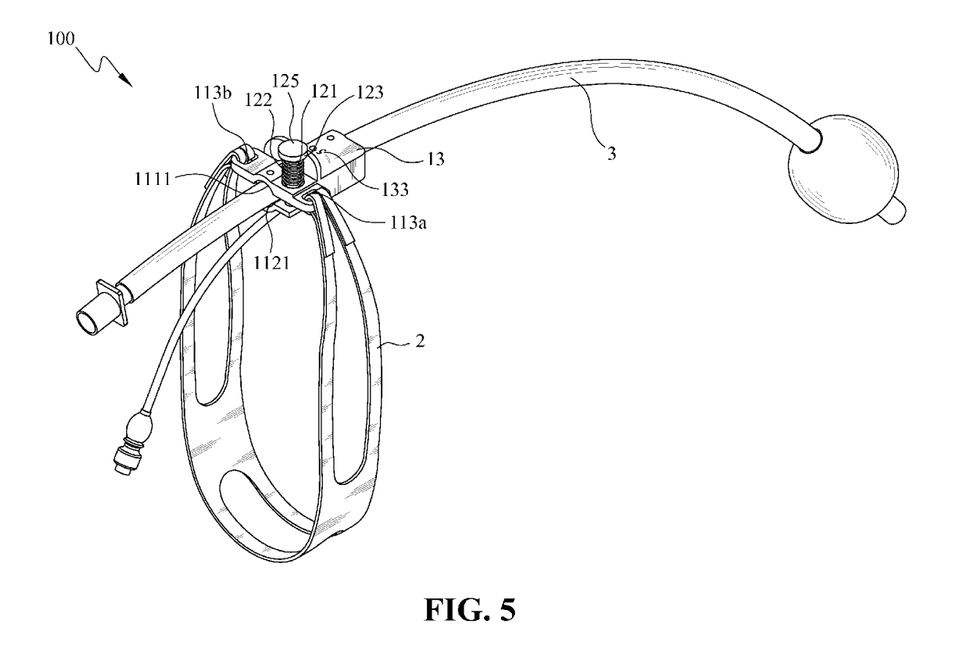
FIG. 5 is a perspective view of FIG. 4 viewing from the opposite side.
Figure 6:
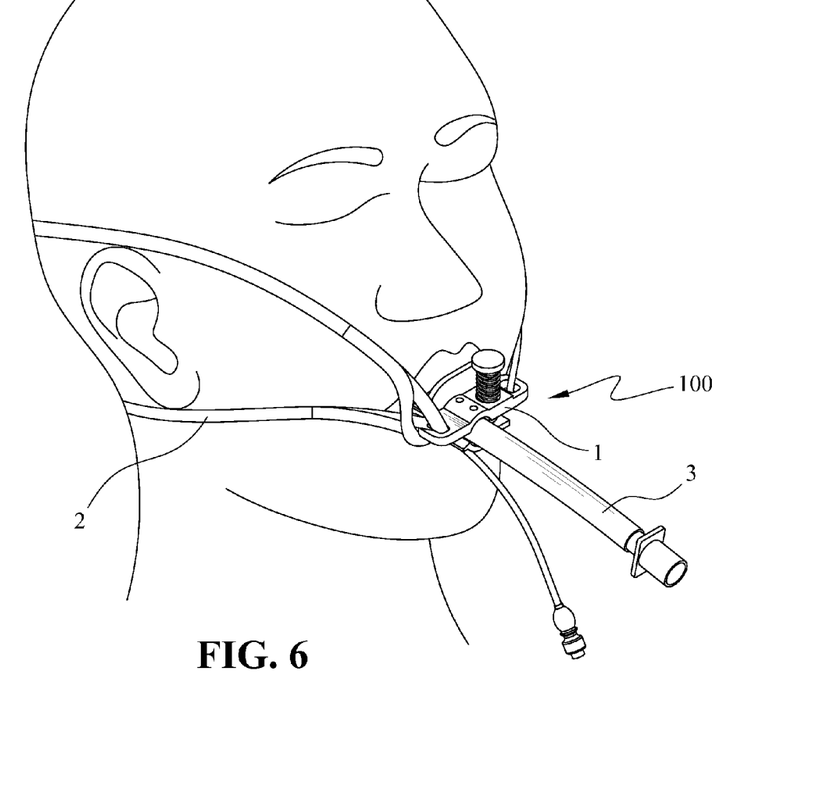
FIG. 6 is a schematic diagram illustrating the operation of the endotracheal tube holder according to an embodiment of the present invention.
Figure 7:
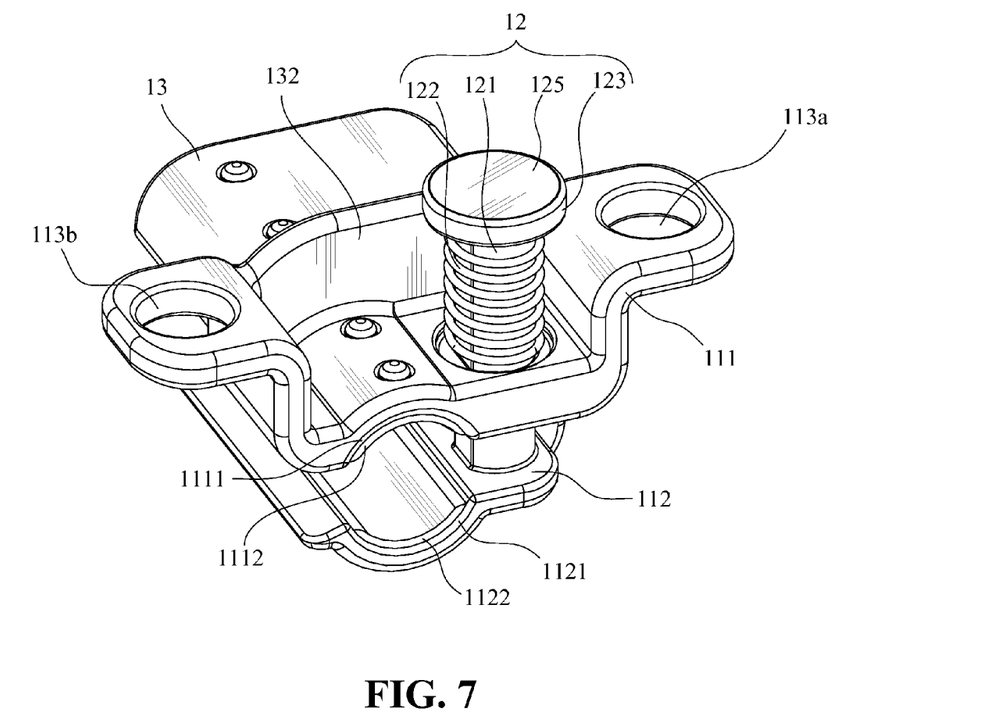
FIG. 7 is a partial enlarged perspective view of the endotracheal tube holder according to another embodiment of the present invention.

FIG. 1 is an exploded view of an adjustable securing clamp of the endotracheal tube holder according to an embodiment of the present invention. FIG. 2 is a perspective view of the endotracheal tube holder according to a preferred embodiment of the present invention. FIG. 3 is a partial enlarged perspective view of the endotracheal tube holder according to a preferred embodiment of the present invention. FIG. 4 is a perspective view of the endotracheal tube holder holding an endotracheal tube. FIG. 5 is a perspective view of FIG. 4 viewing from the opposite side. FIG. 6 is a schematic diagram illustrating the operation of the endotracheal tube holder according to an embodiment of the present invention. FIG. 7 is a partial enlarged perspective view of the endotracheal tube holder according to another embodiment of the present invention. Referring to FIGS. 1-7, there is shown an endotracheal tube holder 100.

The endotracheal tube holder 100 of the present invention comprises an adjustable securing clamp 1 (as shown in FIG. 1) and a securing strap 2 (as shown in FIG. 2). In principle, the adjustable securing clamp 1 shown in FIG. 1 comprises a first clamping unit 111 and a second clamping unit 112. The first clamping unit has a first clamping portion 1111. The first clamping portion 1111 has two lateral wings, on which two through holes 113a and 113b are configured respectively. The second clamping unit 112 has a second clamping portion 1121. Referring to FIGS. 1 and 3 together, the first clamping portion 1111 has an arcuate surface adapted for matching with an outer surface of an endotracheal tube 3 to be secured by the adjustable securing clamp 1. The second clamping portion 1121 also has an arcuate surface adapted for matching with the outer surface of the endotracheal tube 3 to be secured by the adjustable securing clamp 1. Specifically, the arcuate surface of the first clamping portion 1111 and the arcuate surface of the second clamping portion 1121 are oppositely and correspondingly configured, and are adapted to be correspondingly aligned with each other for holding an endotracheal tube 3, as shown in FIG. 5. Further, the adjustable securing clamp 1 comprises a first pad 1112 and a second pad 1122. The first pad 1112 is assembled to the arcuate surface of the first clamping portion 1111, and the second pad 1122 is assembled to the arcuate surface of the second clamping portion 1121. The first pad 1112 and the second pad 1122 are made of an elastic material, preferably medical silicone material.

Referring to FIGS. 1 and 2, the adjustable securing clamp 1 comprises an adjusting unit 12. The adjusting unit 12 is a push-on type spring adjusting unit includes a pushing rod 121, and an elastic member (preferably a spring 122). The pushing rod 121 has a first end and a second end. The first end of the pushing rod 121 is secured to the second clamping unit 112, and the second end of the pushing rod 121 is inserted through a through hole 114 of the first clamping unit 111 and the spring 22. The second end of the pushing rod 121 is coupled with a pushing button 123. A sticker 125 is provided on the pushing button 123 for dimensioning. The sticker 125 for example can be but is not limited to be a black aluminum-like printed button sticker. The pushing button 123 is configured with a central through hole. A screw 124 is provided through the central through hole of the pushing button 123 for locking the pushing button 123 to the second end of the pushing rod 121. The spring 122 is positioned between the pushing button 123 and the first clamping unit 111.

The adjustable securing clamp 1 further comprises a bite block 13. Preferably, the bite block 13 is integrally formed together with the first clamping unit 111, and is configured at one side of the first clamping unit 111, as shown in FIG. 1. A bite wall 132 is provided between the bite block 13 and the first clamping unit 111 for preventing the patient's mouth from touching the elastic member or the spring 122. Referring to FIG. 4, the bite block 13 has an endotracheal tube accommodation portion 131. The endotracheal tube accommodation portion 131 has an arcuate surface adapted for matching with and covering over an outer surface of the endotracheal tube 3 for providing a further protection to the endotracheal tube 3. The arcuate surface of the endotracheal tube accommodation portion 131 joins with the arcuate surface of the first clamping portion 1111. Preferably, the bite block 13 is transparent or translucent. Further, an upper surface of the first pad 1112 comprises at least one mark 133 marked at a teeth positioning position. According to one aspect of the embodiment, the first pad 1112 is assembled under the arcuate surface of the first clamping portion 1111, such that the mark 133 is visibly displayed on the bite block 13. Alternatively, at least one mark is marked at a teeth positioning position of an upper surface of the bite block 13.

Referring to FIG. 5, the endotracheal tube holder 100 comprises the adjustable securing clamp 1 and the securing strap 2. The endotracheal tube holder 100 is particularly adapted for clamping to secure the endotracheal tube 3, after the endotracheal tube 3 is inserted, so as to prevent the endotracheal tube 3 from being accidentally dropped off and avoiding unplanned extubation executed by the patient himself.

In accordance with one embodiment of the present invention, the bite block 13 is made of a plastic material such as polypropylene (PP), acrylonitrile butadiene styrene (ABS), or polycarbonate (PC). The bite block 13 is configured at one lateral side of the first clamping portion 1111. The endotracheal tube accommodation portion 131 of the bite block 13 is configured with an up-down structure for accommodating and covering the endotracheal tube 3 inside the patient's mouth cavity. Comparing with the conventional technology, the bite block 13 not only covers the endotracheal tube 3, but also facilitates to secure the endotracheal tube 3 and prevents the endotracheal tube 3 from being bitten by the patient, thus eliminating the need for employing the oral airway.

Regarding the materials employed in the embodiment of the present invention, outer surfaces of the first clamping unit 111 and the second clamping unit 112 of the adjustable securing clamp 1 are coated with a silicon layer, and the bodies of the first clamping unit 111 and the second clamping unit 112 of the adjustable securing clamp 1 are substantially constituted of plastic materials, such as PP, ABS and PC. In accordance with the materials selected for making the adjustable securing clamp 1, the endotracheal tube holder 100 is less likely to cause ulcer in mouth cavity of the patient, and the endotracheal tube holder 100 is pressure-resistant and less likely to be broken. After being cleaned and sterilized, the endotracheal tube holder 100 can be reused. If otherwise, the endotracheal tube holder 100 is not desired to be reused, it is disposable.

With respect to the securing strap 2, it is constituted of an outer silicon layer and an inner cotton layer. Comparing with the cotton string used by the prior art, the securing strap 2 adopts a composite material which is more elastic and more comfortable, and is less likely to cause skin allergy, compression on the corners of patient's mouth, or injuries to skins behind ears. Further, in accordance with another embodiment of the present invention, the securing strap 2 is configured with a nonwoven fabric layer outer layer. The nonwoven fabric outer layer is preferred to be but not restricted to be a velvet material. The nonwoven fabric layer is further provided with a corresponding Velcro member (not shown in the drawings) at two lateral sides of the first clamping unit 111. Incorporated with the two sides of the first clamping unit 111, the securing strap 2 can be conveniently adjusted to achieve a suitable length by a fast adhesion operation between the nonwoven fabric layer and the Velcro member.

In operation, the operation staff can conveniently operate the endotracheal tube holder 100. For example, when the operation staff applies a force on the pushing button 123 of the pushing rod 121, the corresponding alignment of the first clamping portion 1111 and the second clamping portion 1121 can be elastically adjusted. When the operation staff subsequently releases the pushing button 123, the first clamping portion 1111 and the second clamping portion 1121 then cooperatively clamp to secure the endotracheal tube 3. In accordance with the present invention, the first clamping portion 1111 and the second clamping portion 1121 are positioned outside the mouth cavity of the patient, thus avoiding clamping to injure tissues inside the mouth cavity.

In accordance with the embodiment, the present invention is particularly adapted for one hand operation, in which the operation staff can use one hand to operate the pushing button 123 of the pushing rod 121 to dismiss the elastic alignment between the first clamping portion 1111 and the second clamping portion 1121, so as to allow adjusting the position of the endotracheal tube 3. The operation of the endotracheal tube holder 100 of the present invention is easy and convenient. Further, as shown in FIG. 7, another embodiment of the present invention, the first clamping unit 111 has two lateral wings with upside-down L shape. The upside-down L shape wings can make the operation staff very conveniently operates the endotracheal tube holder 100 for one hand operation.

Referring to FIG. 6, the first clamping unit 111 has two lateral wings, on which two through holes 113a and 113b are configured respectively. The two ends of the securing strap 2 are inserted therethrough and secured thereto, thus forming a loop structure. The loop structure is adapted for bridling the patient's head, so as to more stably secure the endotracheal tube 3.

Further, as shown in FIG. 6, the securing strap 2 has two sections (upper section and lower section as shown in FIG. 6). After bridling the patient's head, the two sections are moved apart along the back of the patient's head, so as to disperse the pressure that the securing strap 2 applied on the patient's head and increase the stability of the endotracheal tube 3 secured in the patient's mouth cavity. Furthermore, the present invention also provides convenience of oral care, and reduces the possibility of bacterial infection caused thereby.

Although the present invention has been described with reference to the preferred embodiments thereof, it is apparent to those skilled in the art that a variety of modifications and changes may be made without departing from the scope of the present invention which is intended to be defined by the appended claims.

What is claimed is:

1. An endotracheal tube holder, comprising:
an adjustable securing clamp, comprising:
a first clamping unit having a first clamping portion;
a second clamping unit having a second clamping portion, wherein the first clamping portion and the second clamping portion are oppositely and correspondingly aligned with each other for holding an endotracheal tube;
an adjusting unit comprising an elastic member coupled between the first clamping unit and the second clamping unit, adapted for providing an elastic adjustment between the corresponding alignment of the first clamping portion and the second clamping portion, wherein the adjusting unit is a push-on type spring adjusting unit comprising a pushing rod and the elastic member, a first end of the pushing rod is secured to the second clamping unit, and a second end of the pushing rod is assembled through a through hole of the first clamping unit, a pushing button is provided at the second end of the pushing rod, and the elastic member is provided between the pushing button and the first clamping unit; and a bite block configured at one side of the first clamping portion, the bite block having an endotracheal tube accommodation portion attaching to and covering over the endotracheal tube for providing a further protection to the endotracheal tube; and a securing strap having two ends, wherein the two ends of the securing strap are respectively coupled to two lateral sides of the first clamping unit.

2. The endotracheal tube holder as claimed in claim 1, wherein the elastic member is a spring.

3. The endotracheal tube holder as claimed in claim 1, wherein an upper surface of the bite block comprises at least one mark marked at a teeth positioning position.

4. The endotracheal tube holder as claimed in claim 1, wherein the endotracheal tube accommodation portion of the bite block is configured with an up-down structure for accommodating and covering the endotracheal tube.

5. The endotracheal tube holder as claimed in claim 1, wherein the securing strap is configured with a silicon outer layer.

6. The endotracheal tube holder as claimed in claim 1, wherein the securing strap is configured with a nonwoven fabric outer layer.

7. The endotracheal tube holder as claimed in claim 1, wherein the securing strap is configured with a cotton inner layer.

8. The endotracheal tube holder as claimed in claim 1, wherein the two ends of the securing strap are respectively coupled to the two lateral sides of the first clamping unit by a hook-and-loop fastener.

9. The endotracheal tube holder as claimed in claim 1, wherein the first clamping unit, the second clamping unit, and the bite block are configured with silicon outer layers, respectively.

10. The endotracheal tube holder as claimed in claim 1, wherein the first clamping unit, the second clamping unit, and the bite block are made of a plastic material.

11. The endotracheal tube holder as claimed in claim 10, wherein the plastic material is polypropylene (PP), acrylonitrile butadiene styrene (ABS), or polycarbonate (PC).

12. The endotracheal tube holder as claimed in claim 1, wherein the bite block is transparent or translucent.

13. The endotracheal tube holder as claimed in claim 1, wherein the adjustable securing clamp further comprises a first pad and a second pad, and the first pad is assembled to the first clamping portion and the second pad is assembled to the second clamping portion.

14. The endotracheal tube holder as claimed in claim 13, wherein the bite block is transparent or translucent, and when an upper surface of the first pad comprises at least one mark marked at a teeth positioning position, the mark is visibly displayed on the bite block.

15. The endotracheal tube holder as claimed in claim 1, wherein the adjusting unit is adapted for one hand operation.

16. An endotracheal tube holder, comprising:
an adjustable securing clamp, comprising:
a first clamping unit having a first clamping portion;
a second clamping unit having a second clamping portion, wherein the first clamping portion and the second clamping portion are oppositely and correspondingly aligned with each other for holding an endotracheal tube;
an adjusting unit comprising an elastic member coupled between the first clamping unit and the second clamping unit, adapted for providing an elastic adjustment between the corresponding alignment of the first clamping portion and the second clamping portion; and a bite block configured at one side of the first clamping portion, the bite block having an endotracheal tube accommodation portion attaching to and covering over the endotracheal tube for providing a further protection to the endotracheal tube, wherein the bite block is transparent or translucent, and when an upper surface of the first pad comprises at least one mark marked at a teeth positioning position, the mark is visibly displayed on the bite block;

a first pad;

a second pad, wherein the first pad is assembled to the first clamping portion and the second pad is assembled to the second clamping portion; and a securing strap having two ends, wherein the two ends of the securing strap are respectively coupled to two lateral sides of the first clamping unit.

17. The endotracheal tube holder as claimed in claim 16, wherein the elastic member is a spring.

18. The endotracheal tube holder as claimed in claim 16, wherein an upper surface of the bite block comprises at least one mark marked at a teeth positioning position.

19. The endotracheal tube holder as claimed in claim 16, wherein the endotracheal tube accommodation portion of the bite block is configured with an up-down structure for accommodating and covering the endotracheal tube.

20. The endotracheal tube holder as claimed in claim 16, wherein the securing strap is configured with a silicon outer layer.

21. The endotracheal tube holder as claimed in claim 16, wherein the securing strap is configured with a nonwoven fabric outer layer.

22. The endotracheal tube holder as claimed in claim 16, wherein the securing strap is configured with a cotton inner layer.

23. The endotracheal tube holder as claimed in claim 16, wherein the two ends of the securing strap are respectively coupled to the two lateral sides of the first clamping unit by a hook-and-loop fastener.

24. The endotracheal tube holder as claimed in claim 16, wherein the first clamping unit, the second clamping unit, and the bite block are configured with silicon outer layers, respectively.

25. The endotracheal tube holder as claimed in claim 16, wherein the first clamping unit, the second clamping unit, and the bite block are made of a plastic material.

26. The endotracheal tube holder as claimed in claim 25, wherein the plastic material is polypropylene (PP), acrylonitrile butadiene styrene (ABS), or polycarbonate (PC).

27. The endotracheal tube holder as claimed in claim 16, wherein the bite block is transparent or translucent.

28. The endotracheal tube holder as claimed in claim 16, wherein the adjusting unit is adapted for one hand operation.

* * * * *